US008043248B2

(12) United States Patent  
Pasricha

(10) Patent No.: US 8,043,248 B2
(45) Date of Patent: Oct. 25, 2011

(54) METHOD FOR SECURING A BARRIER DEVICE WITHIN THE GASTROINTESTINAL TRACT AND INTEGRAL COMPONENT FOR SAME

(75) Inventor: Pankaj Jay Pasricha, Cupertino, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 387 days.

(21) Appl. No.: 12/416,932

(22) Filed: Apr. 2, 2009

(65) Prior Publication Data

US 2010/0256654 A1 Oct. 7, 2010

(51) Int. Cl.
*A61M 5/00* (2006.01)
*A61B 17/00* (2006.01)
(52) U.S. Cl. .................... 604/8; 604/9; 606/139
(58) Field of Classification Search ............. 604/8–10, 604/96.01; 600/37; 606/151, 191; 623/23.64–23.68
See application file for complete search history.

(56) References Cited

U.S. PATENT DOCUMENTS

| 7,025,791 | B2* | 4/2006 | Levine et al. ............. 623/23.64 |
| 7,074,229 | B2 | 7/2006 | Adams et al. |
| 7,288,101 | B2 | 10/2007 | Deem et al. |
| 2004/0243152 | A1 | 12/2004 | Taylor et al. |
| 2004/0249362 | A1 | 12/2004 | Levine et al. |
| 2005/0055038 | A1 | 3/2005 | Kelleher et al. |
| 2005/0075653 | A1 | 4/2005 | Saadat et al. |
| 2005/0075654 | A1 | 4/2005 | Kelleher |
| 2005/0192615 | A1 | 9/2005 | Torre et al. |
| 2007/0135825 | A1* | 6/2007 | Binmoeller ............ 606/153 |
| 2008/0125797 | A1 | 5/2008 | Kelleher |
| 2008/0200930 | A1 | 8/2008 | Saadat et al. |

FOREIGN PATENT DOCUMENTS

WO  WO 2007/038715  4/2007

OTHER PUBLICATIONS

Seaman et al., "Tissue anchors for transmural gut-wall apposition," Gastrointestinal Endoscopy. vol. 64, Issue 4, pp. 577-581 (Oct. 2006) (Abstract of article provided, sheets 1-3).
Kuroiwa et al., "Usefulness of Introducer Technique Combined with a Commercially Available Anchoring Device for Percutaneous Endoscopic Gastrostomy," Pediatric Endosurgery and Innovative Techniques. vol. 6, Issue 1, pp. 35-40 (2002). (Brief paper of article provided, sheets 1-3).

* cited by examiner

*Primary Examiner* — Leslie Deak
*Assistant Examiner* — Philip Wiest
(74) *Attorney, Agent, or Firm* — Neal Marcus

(57) ABSTRACT

A method is disclosed for creating an anchor within the gastrointestinal tract for supporting a barrier device therein. The gastrointestinal tract has a first wall, a second wall and a body lumen. The method comprises advancing an anchoring device through the first wall and the second wall, threading the barrier device over the anchoring device and advancing the barrier device into the body lumen, and forming a closed loop with the anchoring device for supporting the barrier device.

9 Claims, 17 Drawing Sheets

METHOD FOR SECURING A BARRIER DEVICE WITHIN THE GASTROINTESTINAL TRACT AND INTEGRAL COMPONENT FOR SAME

FIELD OF THE INVENTION

The present invention relates to method of securing a barrier device within the gastrointestinal tract and an integral component for the same.

BACKGROUND OF THE INVENTION

It estimated that almost twenty four million people in the United States have diabetes. The most common form of diabetes is type 2 diabetes. In adults, 90 to 95% of the people with diabetes have type 2 diabetes. Type 2 diabetes is a chronic condition that affects the way the body metabolizes sugar (glucose), the body's main source of fuel. With type 2 diabetes, the body is resistant to the effects of insulin or the body produces some insulin, but in insufficient amounts to maintain a normal glucose level. This is known as insulin resistance. (Insulin is a hormone that regulates the absorption of sugar into the body.) If type 2 diabetes is left untreated, the consequences can be deadly. Unfortunately, type 2 diabetes is on the rise. This is fueled largely by the current obesity epidemic.

In recent years, the medical community has made inroads in the fight against type 2 diabetes. Specifically, gastric bypass studies in rats and humans have shown that an endoscopically implanted barrier device such as a sleeve within the lumen of the duodenum causes a marked reduction in insulin dependence and hence a greater improvement in the control of type 2 diabetes. In short, the sleeve acts as a barrier to prevent nutrients from being absorbed by the lining of the duodenum. Current methods for securing the barrier sleeve within the lumen involve anchoring the device to the wall of the gastrointestinal tract. In this approach, the sleeve is actually implanted into tissue of the wall using clips, sutures, struts, barbs or other implantable anchoring devices. However, this method of securing the sleeve has not been effective over the long term. In some circumstances, the sleeve has dislodged after implantation and has migrated down into the gastrointestinal tract. In other circumstances, the specific areas in which the sleeve is implanted have become inflamed, and removal has become difficult. Dislodgement and/or inflammation cause serious complications for the patient.

It would be therefore desirable to offer a solution that would overcome the disadvantages of the method described above.

SUMMARY OF THE INVENTION

In accordance with an embodiment of the present invention, a method is disclosed for creating an anchor within the gastrointestinal tract for supporting a barrier device therein. The gastrointestinal tract has a first wall, a second wall and a body lumen. The method comprises advancing an anchoring device through the first wall and the second wall, threading the barrier device over the anchoring device and advancing the barrier device into the body lumen, and forming a closed loop with the anchoring device for supporting the barrier device.

In accordance with another embodiment of the present invention, a method is disclosed for creating an anchor within the gastrointestinal tract for supporting a barrier device therein. The gastrointestinal tract has a stomach and duodenum, each having a wall defining a lumen. The method comprises advancing an anchoring device through the duodenum wall and the stomach wall, threading the barrier device over the anchoring device and advancing the barrier device into the duodenum lumen, and forming a closed loop with the anchoring device for supporting the barrier device within the duodenum lumen.

In accordance with another embodiment of the present invention, a method is disclosed for creating an anchor within the gastrointestinal tract for supporting a sleeve, the gastrointestinal tract having a stomach and duodenum, each having a lumen and a wall. The method comprises introducing a guide wire through the duodenum wall and stomach wall, advancing an anchoring device over the guide wire through the stomach wall and the duodenum wall, threading the sleeve over the anchoring device and advancing the sleeve into the duodenum lumen, and forming a closed loop with the anchoring device for supporting the sleeve within the duodenum lumen.

In accordance with another embodiment of the present invention, a method is disclosed for creating an anchor within the gastrointestinal tract for supporting a barrier device therein. The gastrointestinal tract has a first wall, a second wall and a body lumen. The method comprises advancing an integral component through the first wall and the second wall, the integral component being configured to include the barrier device and an anchoring device, advancing the integral component to position the barrier device within the body lumen, and forming a closed loop with the anchoring device for supporting the barrier device within the body lumen.

In accordance with yet another embodiment of the present invention, an integral component is disclosed that is adapted to be delivered within a body. The component comprises a barrier device for preventing the absorption of food products within a body lumen of the body and an anchoring device for supporting the barrier device within the body lumen.

DETAILED DESCRIPTION

Figure 1:
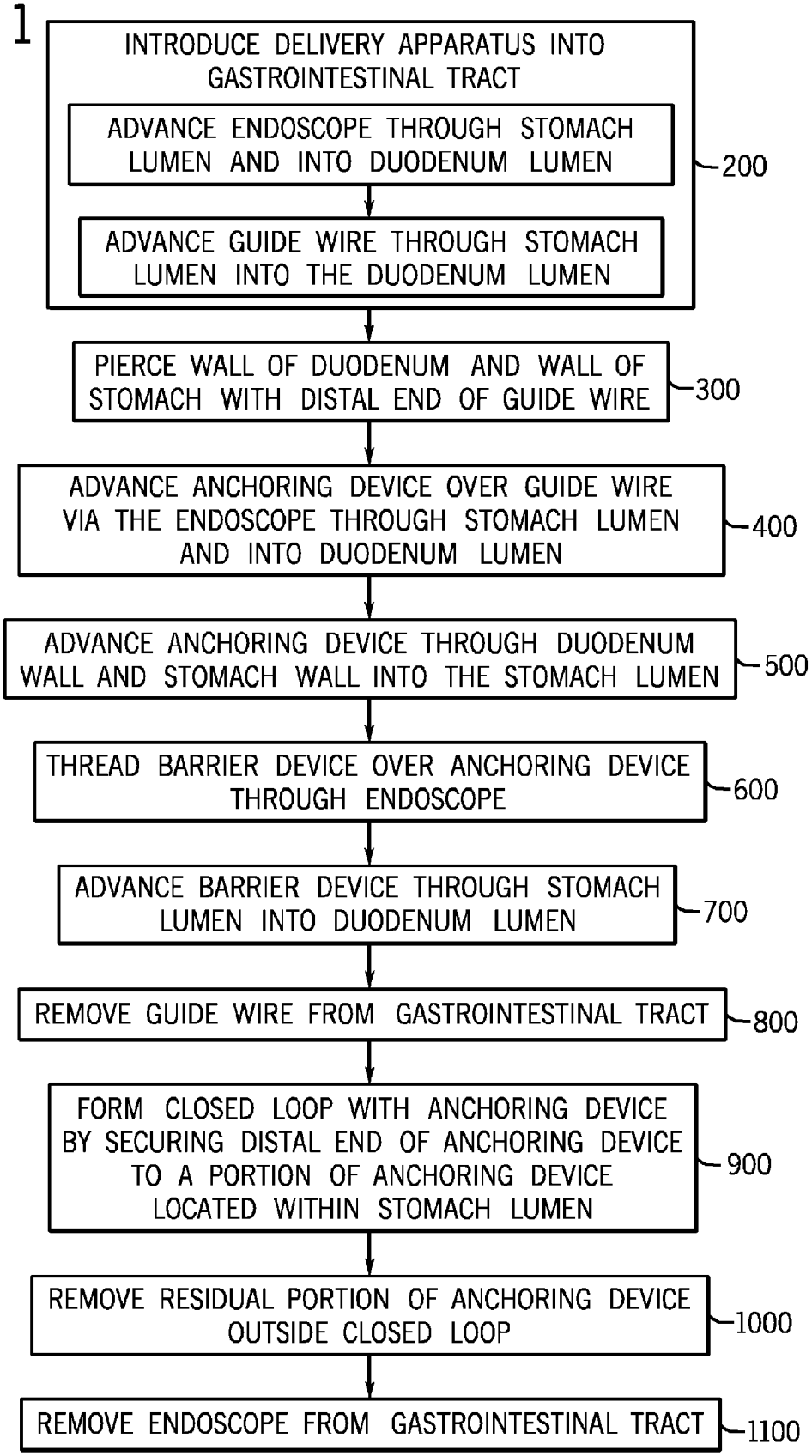
FIG. 1 depicts a block diagram of the steps of the method of securing a barrier device within the gastrointestinal tract in accordance with present invention.

FIG. 1 depicts a block diagram of the steps of the method for securing a barrier sleeve within the gastrointestinal tract. FIGS. 2-12 depict cross-sectional views of the gastrointestinal tract corresponding to the steps of the method shown in FIG. 1, and such FIGS. 2-12 will be discussed as they correspond to the steps of the method depicted in FIG. 1.

In accordance with one illustrative embodiment, steps 200-1100 are performed sequentially, but it will be clear to those skilled in the art, after reading this disclosure, how to make and use alternative embodiments of the present invention in which some of the steps 200-1100 are performed in a different order.

Figure 2:
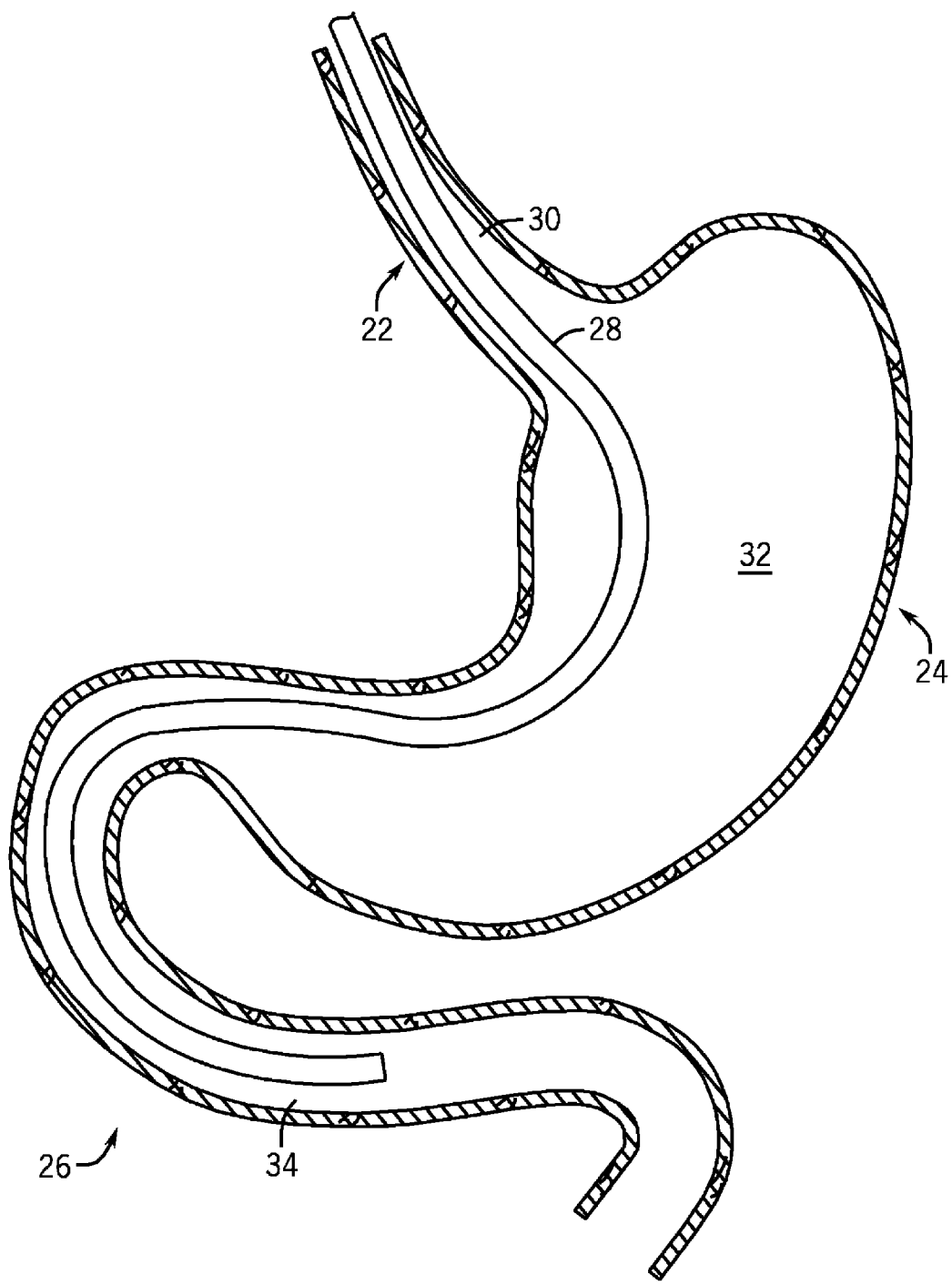
FIGS. 2-12 depict cross-sectional views of the gastrointestinal tract corresponding to the steps of the method depicted in FIG. 1.
Figure 3:
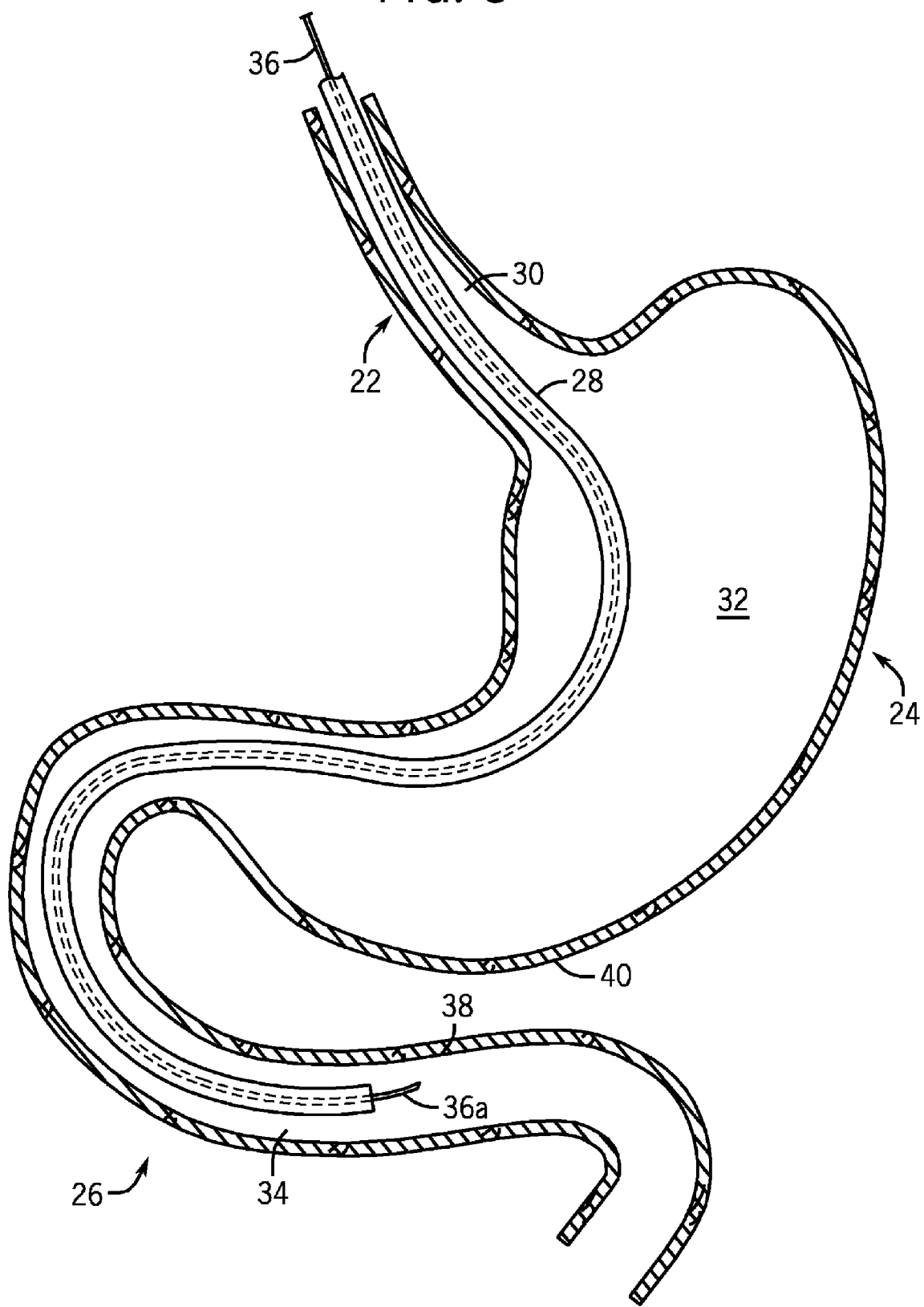

At step 200, a medical doctor (typically a surgeon), will introduce a delivery apparatus into the gastrointestinal tract. Reference is made to FIGS. 2 and 3 in which esophagus 22, stomach 24 and duodenum 26 of the gastrointestinal tract are shown. Note, however, that only a portion of esophagus 22 is shown. As part of step 200, the doctor will advance endoscope 28 into a patient's mouth (not shown), down esophagus lumen 30 through stomach lumen 32, and into duodenum lumen 34. (Esophagus lumen 30, stomach lumen 32, and duodenum lumen 34 are all body lumens of the gastrointestinal tract.) Next, as part of step 200, the doctor will advance guide wire 36 through stomach lumen 32 and into duodenum lumen 34 via endoscope 28. As known to those skilled in the art, endoscope 28 has a lumen that extends from the proximal end (proximate the mouth) to a distal end thereof (proximate the delivery site) for receiving and advancing guide wire 30. Guide wire 36 is actually inserted into endoscope 22 into the lumen thereof for such advancement into the gastrointestinal tract. End 36a of guide wire 36 is shown adjacent the delivery site of duodenum lumen 34 in FIG. 3.

Note that the steps of the method shown in FIG. 1 are described herein as being performed by one doctor, but one skilled in the art will know, after reading this disclosure, that one or more steps of this method may be performed by more than one doctor or medical professional (under the care and supervision of a doctor).

As discussed herein, the introduction of the delivery apparatus includes the step of advancing the endoscope 28 and the guide wire 36. However, those skilled in the art, after reading this disclosure, know that the step of introducing a delivery apparatus disclosed herein may refer to the step of advancing an endoscope or a guide wire individually or in combination, and/or some other device(s) to achieve desired results (i.e., to advance anchoring device 42 and barrier device 44 as discussed below). Such a device(s) may be one or more laparoscopic devices (also known to those skilled in the art) or another device. This is discussed in more detail below.

Figure 4:
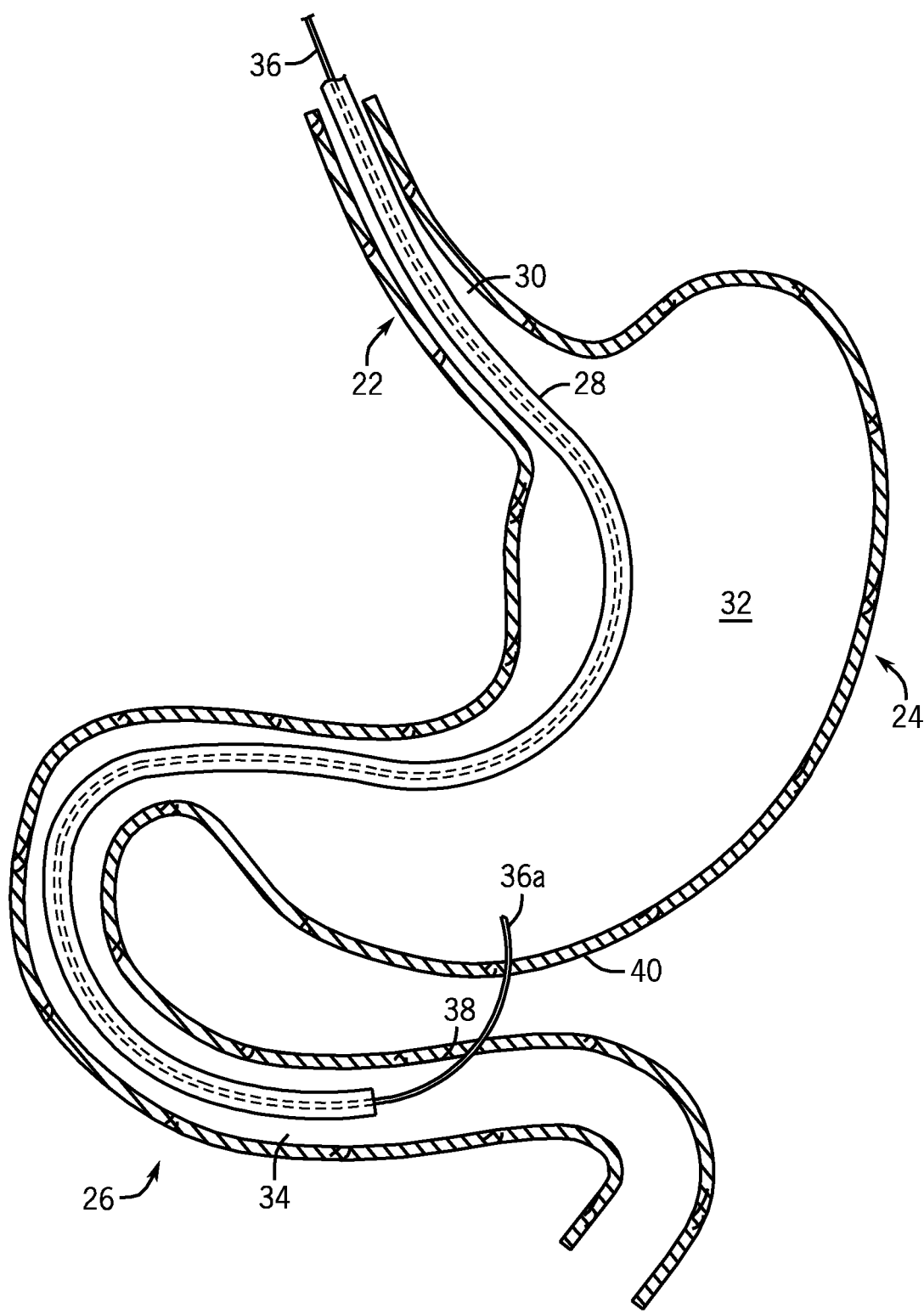

At step 300, the doctor will pierce duodenum wall 36 and then stomach wall 28 with end 36a of guide wire 36. In an alternative embodiment, the doctor may advance a needle along with guide wire 36 to the delivery site for piercing the tissue as is known to those skilled in the art. In FIG. 4, end 36a has pierced duodenum wall 38 and stomach wall 40 and has advanced into stomach lumen 32.

The doctor may not require visualization to pierce the tissue at the appropriate location on the duodenum wall 38. In this respect, the doctor will pierce a hole in the tissue by poking guide wire 36 or needle blindly against the tissue without any visualization, as shown in FIG. 4. However, visualization may be desirable. Visualization may be achieved in several ways to assist the doctor in piercing tissue at the appropriate location along duodenum wall 36 (and stomach wall 38). If the doctor desires direct visualization, he/she will introduce and advance a second endoscope (with appropriate lens/camera technology for visualization) within the gastrointestinal tract. In this respect, the second endoscope will enable the doctor to directly visualize the delivery site and duodenum wall 38.

If direct (sight) visualization is not desired, the doctor has several tools to obtain visualization indirectly. For example, the doctor may use an endoscopic ultrasound device (EUS) to obtain visualization indirectly. The EUS combines endoscopy and ultrasound to obtain images of the gastrointestinal tract to provide visualization of the delivery site as known by those skilled in the art. In yet another alternative embodiment, the doctor may use an X-ray or a CAT scan to enable visualization. Alternatively, the doctor may use trans-reflectance illumination to provide visualization as known to those skilled in the art.

The embodiments described above are merely examples of obtaining visualization (directly or indirectly) to enable a doctor to pierce the appropriate tissue for this procedure. It will be, however, clear to those skilled in the art, after reading this disclosure, how to make and use alternative embodiments of the present invention to achieve visualization.

Figure 5:
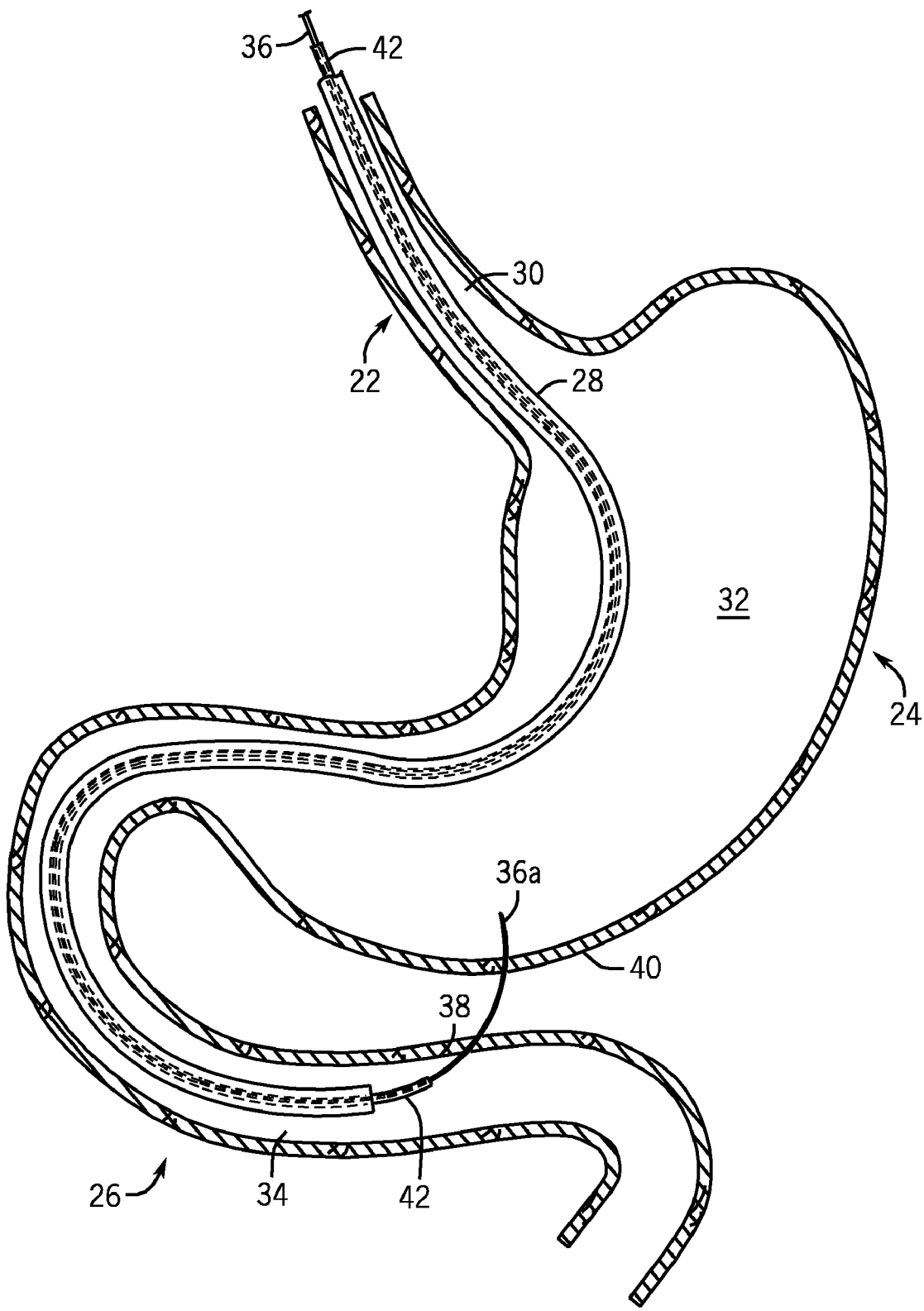

At step 400, the doctor will thread and advance anchoring device 42 over guide wire 36 via endoscope 28 through esophagus lumen 30 and stomach lumen 32 and then into duodenum lumen 34. Anchoring device 42 will be used to anchor a barrier device within duodenum lumen 34 as described in detail below. FIG. 5 illustrates anchoring device 42 in the advanced position but it has not yet passed through duodenum wall 38. In an alternative embodiment, anchoring device 42 may be threaded and advanced over a needle-guide wire combination as described above. Anchoring device 42 is preferably a soft catheter made of atraumatic elastic (stretchable) material such as polyurethane or a combination of latex and silicon materials.

Figure 6:
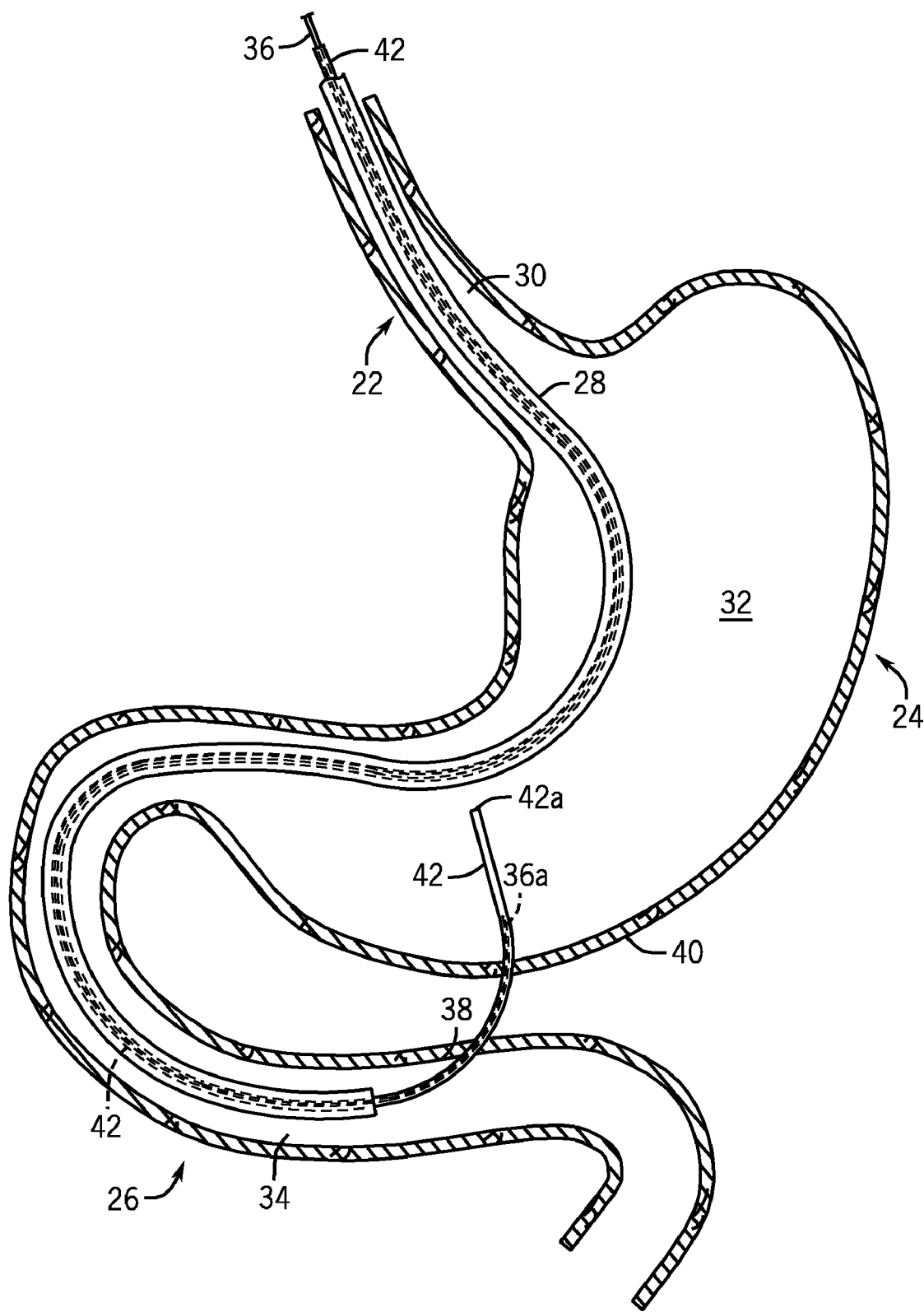

At step 500, the doctor will advance anchoring device 42 through (the openings in) duodenum wall 38, stomach wall 40, and into stomach lumen 32. FIG. 6 illustrates anchoring device 42 in an advanced position through duodenum wall 38 and stomach wall 40. Distal end 42a of anchoring device 42 is shown unattached. In this embodiment of the method described with respect to FIG. 1, note that endoscope 28 is generally held in place to maintain guide wire 36 in place to enable the advancement and delivery of anchoring device 42 and the barrier device 44 (described below) into position.

Figure 7:
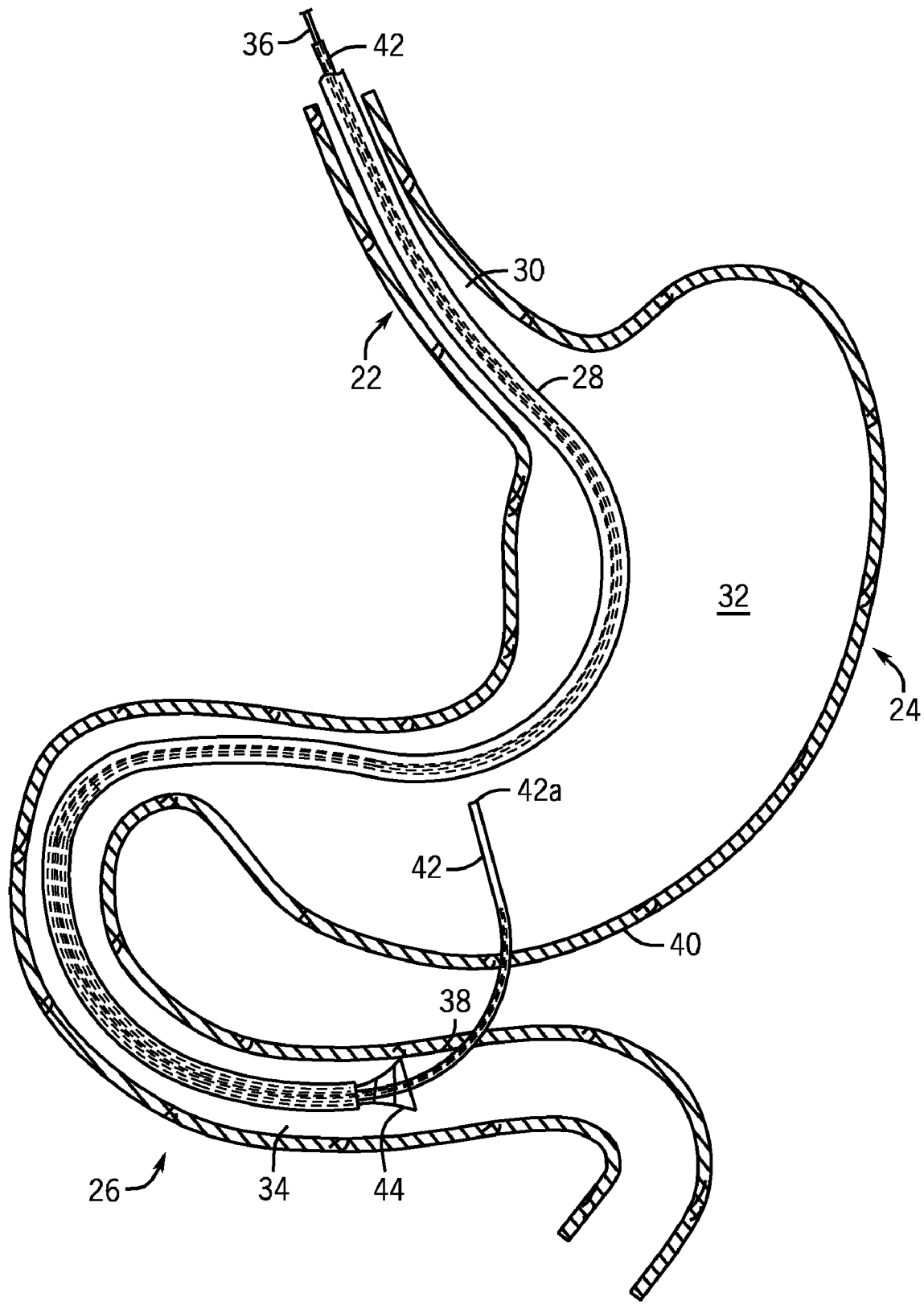
Figure 8:
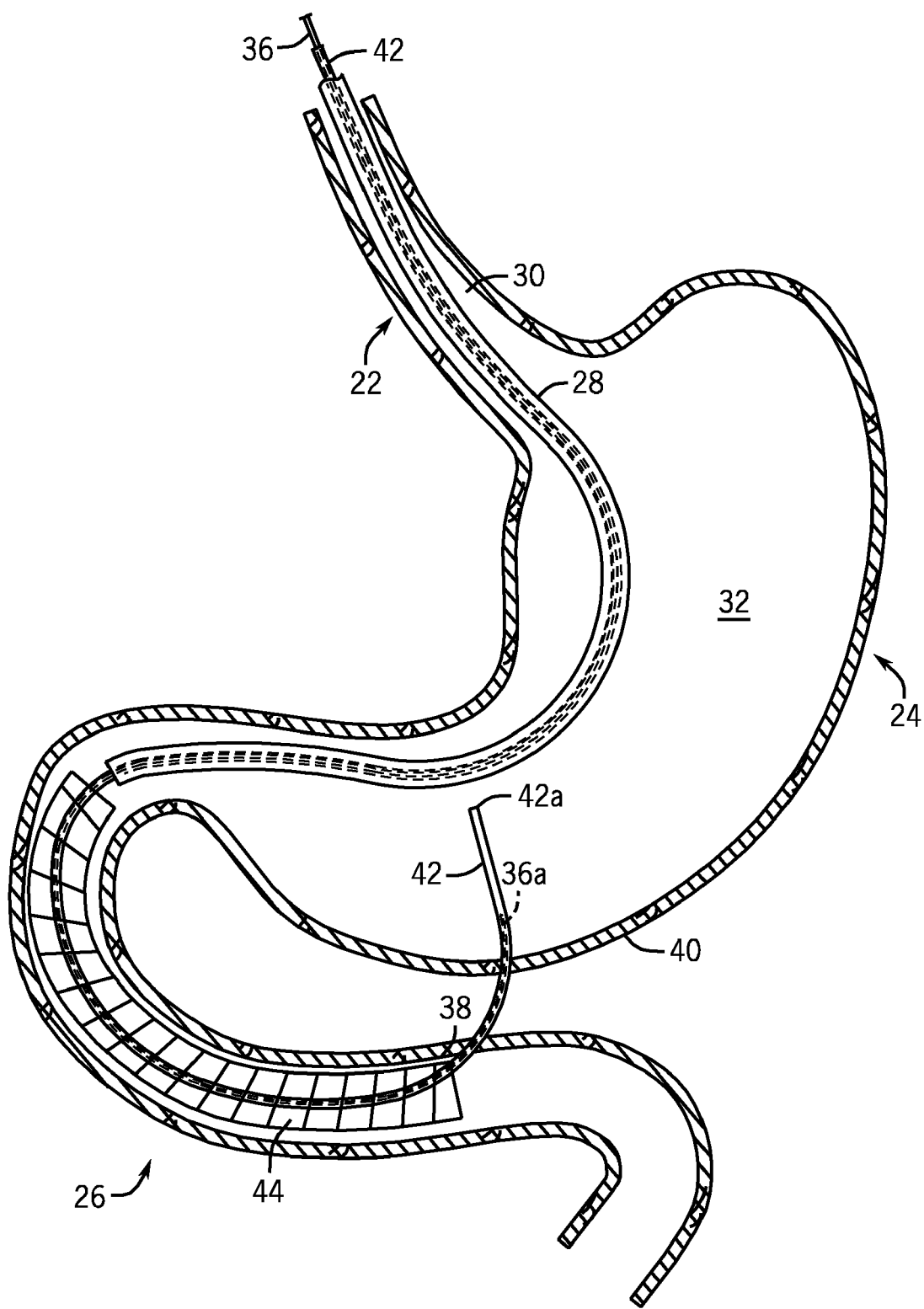

At step 600, the doctor will thread barrier device 44 over anchoring device 42 and guide wire 36 through endoscope 28. Hence, barrier device 44 is advanced through esophagus lumen 30 and stomach 32, and then passed out endoscope 28 to the delivery site within duodenum lumen 34. Barrier device 44 is shown in FIG. 7 partially exiting endoscope 28, and fully deployed in FIG. 8. Barrier device 44 may be advanced through endoscope 28 using (i.e., with the assistance of) a separate collapsible/expandable tube or similar device (not shown). The doctor will advance the tube within endoscope 28 over anchoring device 42 behind barrier device 44 to force it through and out endoscope 28. At the same time, the doctor will begin to withdraw endoscope 28 to allow barrier device 44 to completely exit endoscope 28. In this respect, barrier device 44 is deployed (positioned) to the proper location using endoscope 28 (itself). Alternatively, a doctor may use a second endoscope (not shown) to assist in the deployment from endoscope 28 and proper placement of the barrier device 44.

In this embodiment, barrier device 44 is a flexible sleeve that is self-expanding as it departs from endoscope 28. As known by those skilled in the art, the self-expanding characteristic may be achieved using a stent or other expandable structure that is embedded within the sleeve material. The sleeve can be collapsed into a small enough diameter (typically less than ¼ inch) to enable endoscopic delivery.

In the embodiment of the method described with respect to FIG. 1, the sleeve is maintained in place without any extra assistance while the remaining steps of the method are performed (including forming a closed loop as described below). However, in some other circumstances, a balloon apparatus may be employed within the sleeve to prevent migration while the other remaining steps of the method are performed.

In practice, a second endoscope (not shown) equipped with appropriate balloon apparatus (e.g., a balloon and inflating channel/tube as known by those skilled in the art) will be used to deploy and expand the balloon inside the sleeve to hold the sleeve in place.

The sleeve is constructed of a synthetic material that is typically thin and comfortable as well as a low coefficient of friction (less than 0.20) so that chyme slides easily through it while allowing bile to slide around it. (Chyme is a liquid mass of partially digested food that passes from the stomach through the pyloric sphincter into the duodenum). The sleeve is of low permeability to fluids so that the chyme does not touch duodenum wall 38 and the digestive enzymes do not significantly break down the chyme. The synthetic material is biologically inert and non-irritating to the body tissues. Examples of the materials include polytetrafluoroethylene (ePTFE), a fluoropolymer with a wall thickness of about 0.0006 inches. Another material may be polyethylene with a wall thickness of less than 0.001 inches. Other materials (and thicknesses) may be used as well to achieve desired results. The material may be coated in the inside and/or outside of the sleeve as required.

As described above, the length of the sleeve is selected to bypass duodenum 26. The length, however, is increased to further decrease absorption within duodenum 26 by bypassing a longer section (e.g., including the jejunum of the gastrointestinal tract). The length of the sleeve is variable and dependent on the patient's Body Mass Index (BMI). In practice, the sleeve length ranges from about 10 to 25 centimeters (cm) and width ranges from 8 to 15 millimeters (mm) for delivery within duodenum lumen 34 (typically between the pyloric region of stomach 24 and the jejunum). The typical length of the sleeve is about 20 cm and the width is about 10 millimeters. However, any length and width may be used to achieve desired results as known by those skilled in the art. The sleeve can be marked on the exterior surface thereof to help detect the position and orientation of the sleeve on a fluoroscopic image.

In accordance with one illustrative embodiment, barrier device 44 is a sleeve that is sized, shaped and constructed as described herein, but it will be clear to those skilled in the art, after reading this disclosure, how to make and use alternative embodiments of the present invention in which the type, size, shape and construction (including materials) of barrier device 44 may differ to achieve desired results.

As described above, the sleeve (barrier device 44) is deployed using a separate tube via endoscope 28. However, for sleeves of sufficient size, a doctor may be unable to use an endoscope for actual delivery of the sleeve. In this case, the doctor will remove endoscope 28 and deliver the sleeve over anchoring device 42 as known by those skilled in the art. In this respect, the doctor may use another endoscope with a clamp to push the sleeve down. Alternatively, the doctor may thread and advance a tube over anchoring device 42 to engage and push the sleeve to the delivery site. As indicated above, the procedure provides a treatment approach for type 2 diabetes.

Figure 9:
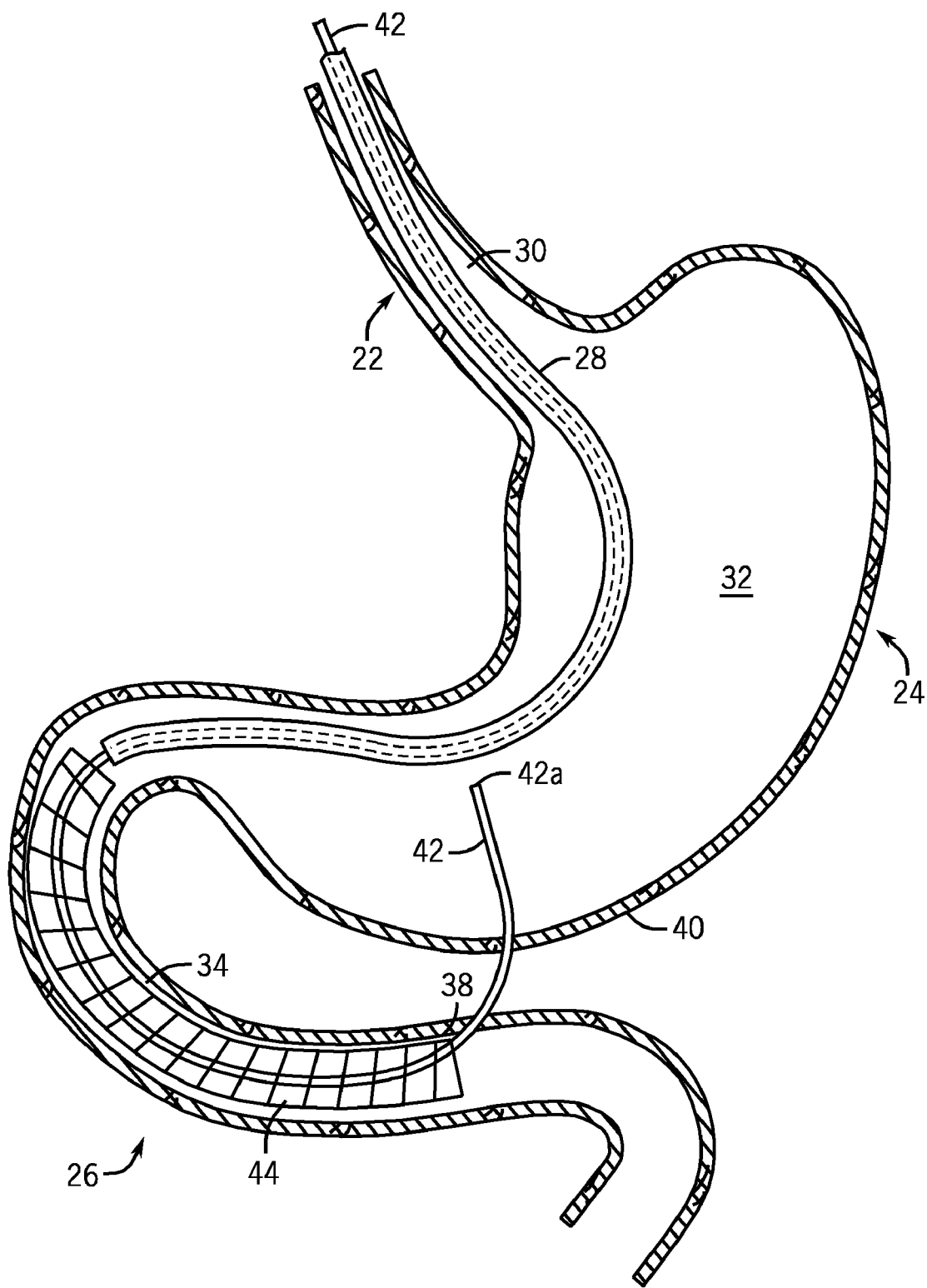

Returning to FIG. 1 wherein step 800 of the method is performed, the doctor removes guide wire 36 from endoscope 28, but the anchoring device 42 remains within the gastrointestinal tract. This is shown in FIG. 9.

Figure 10:
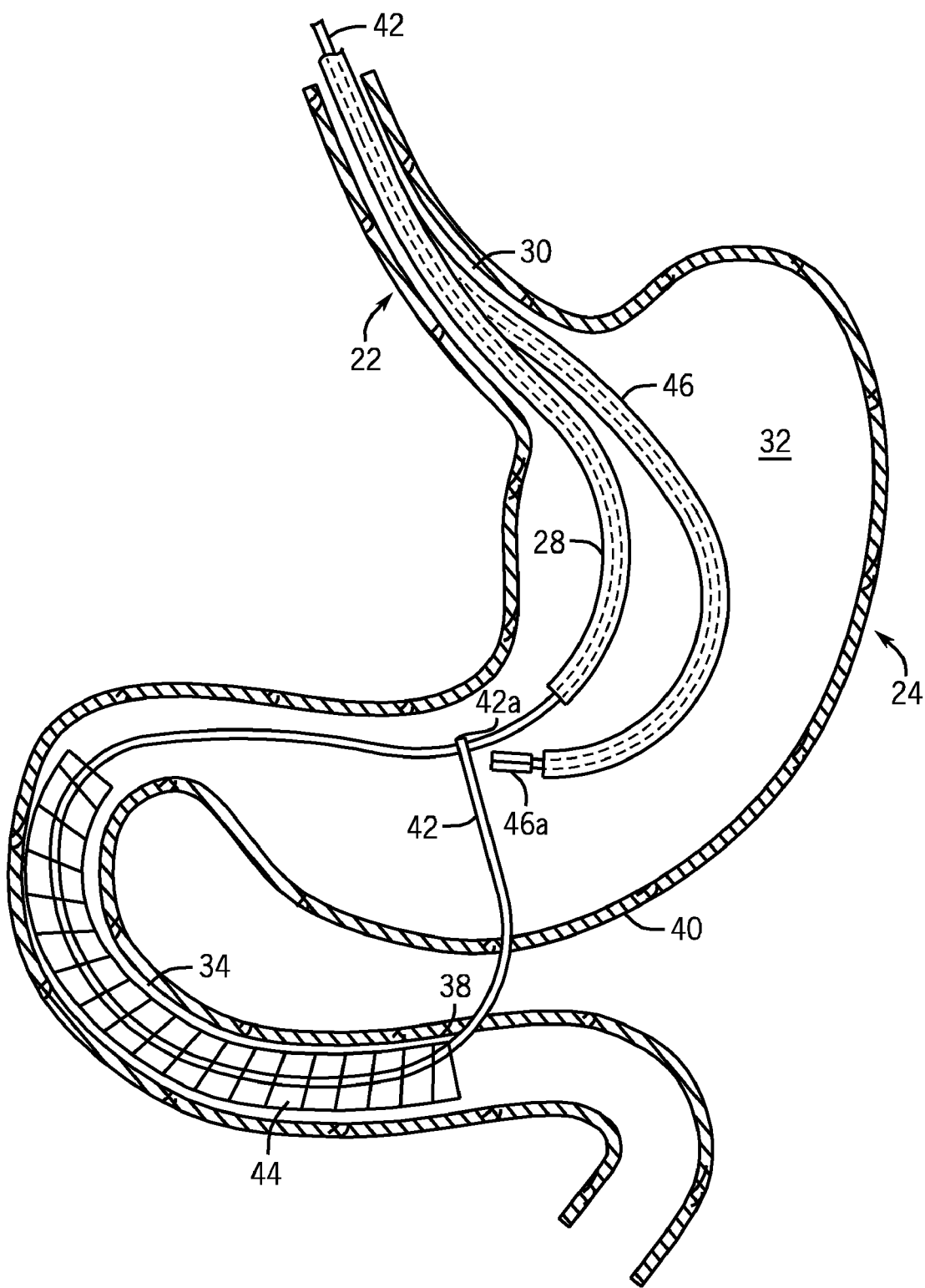

At step 900, a closed loop is formed with anchoring device 42 by securing distal end 42a of anchoring device 42 to a portion thereof within stomach lumen 32. Reference is made to FIG. 10. The doctor performs this step using a second endoscope, i.e., endoscope 46. The doctor introduces endoscope 46 within the gastrointestinal tract in a similar manner as endoscope 28. Note that endoscope 28 is shown retracted or partially withdrawn to expose the necessary portion of anchoring device 42 to enable the doctor to make the closure loop. (In an alternative embodiment, the doctor may remove endoscope 28 entirely at this point, as long as distal end 42a is firmly grasped as described below.)

At this point, the doctor uses a clamping mechanism 46a of endoscope 46, as known to those skilled in the art, to grasp distal end 42a of anchoring device 42. Distal end 46a can be secured to a portion of anchoring device 42 (to form a closed loop or ring) by several methods. In one method, distal end 42a may be secured by a snap on device such as a mechanical clip or clamp such as an "alligator" clamp wherein the jaws may be activated or expanded to receive the anchoring device 42 or a "paper clip" type device. Alternatively, distal end 42a may be secured to anchoring device 42 using cinching device as known by those skilled in the art or an adhesive (e.g., glue or Velcro like material). The glue material may be acrylate for example. On the other hand, distal end 42a may be thermally secured to anchoring device 42 to form a loop. In this respect, distal end 42a will be heated to melt it to anchoring device 42. The closure is all accomplished endoscopically as known by those skilled in the art. (FIGS. 13-16 illustrate alternate steps for obtaining a closed loop by securing the distal end 42a to the body of anchoring device 42. This is discussed below.)

Figure 11:
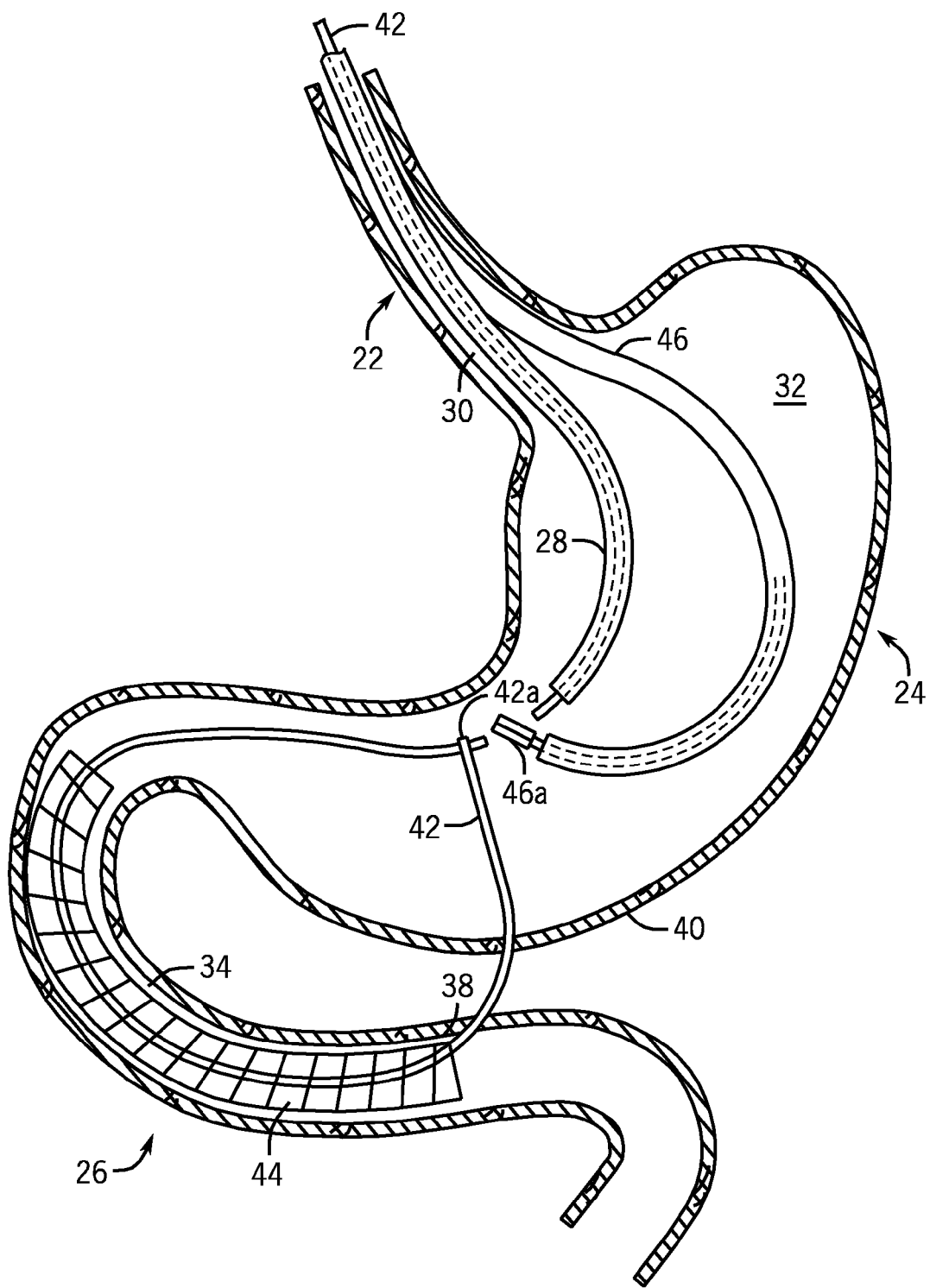

At step 1000, the doctor will remove the residual portion of anchoring device 42 outside of the closed loop, by manipulating the clamping mechanism and clipping the anchoring device 42 above the point at which distal end 42a is secured. This is shown in FIG. 11 (except the remaining part of anchoring device 42 is shown about to be removed). (Note that the clamping mechanism includes the clipping mechanism but a separate clipping mechanism may be employed.)

Figure 12:
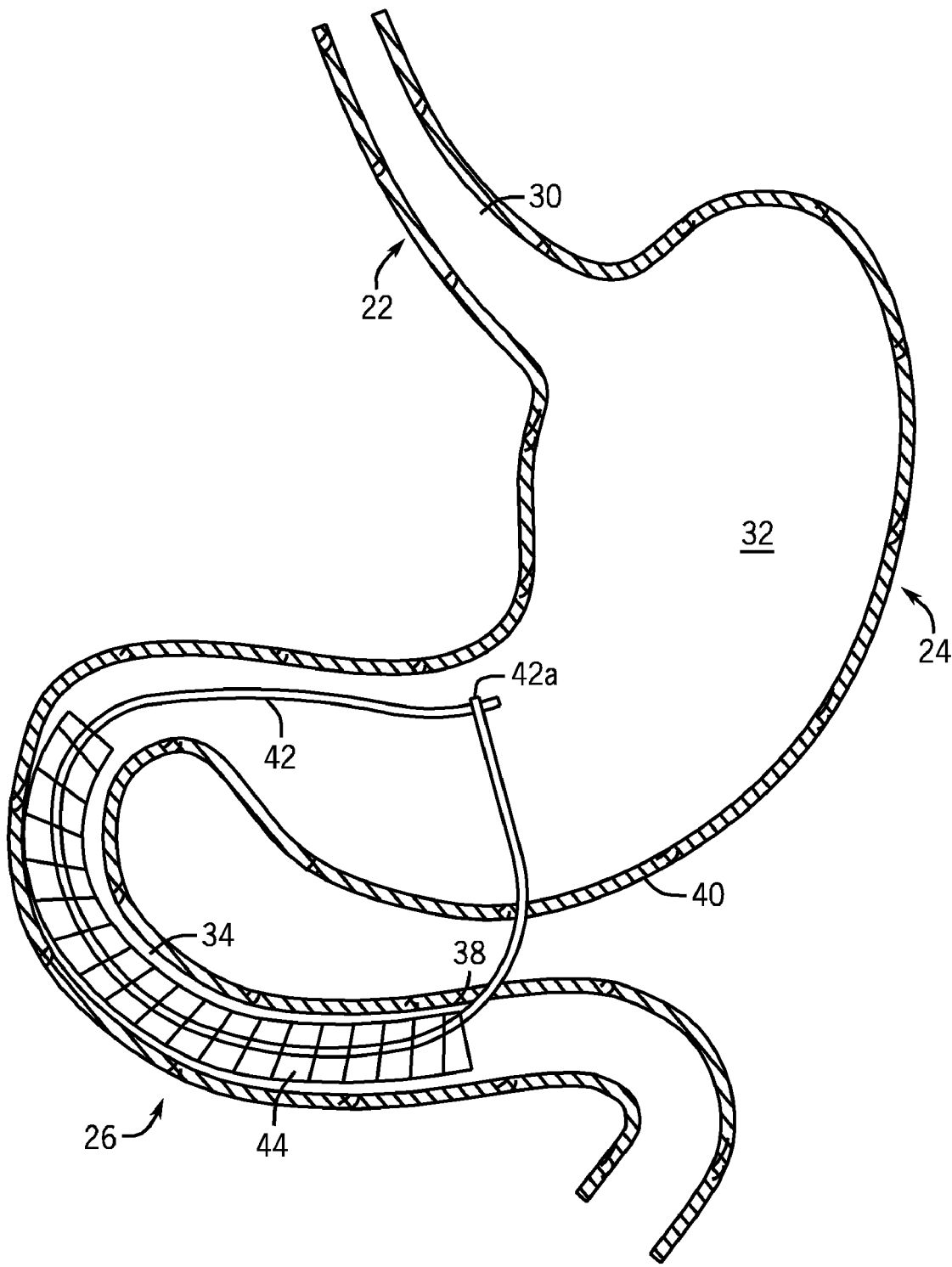

At step 1100, the doctor removes endoscope 28 and endoscope 46 from the gastrointestinal tract of the patient to complete the procedure. The closed loop (of anchoring device 42) is shown in FIG. 12. The tissue surrounding anchoring device 42 within duodenum wall 38 and stomach wall 40 eventually grows around and to anchoring device 42.

Figure 13:
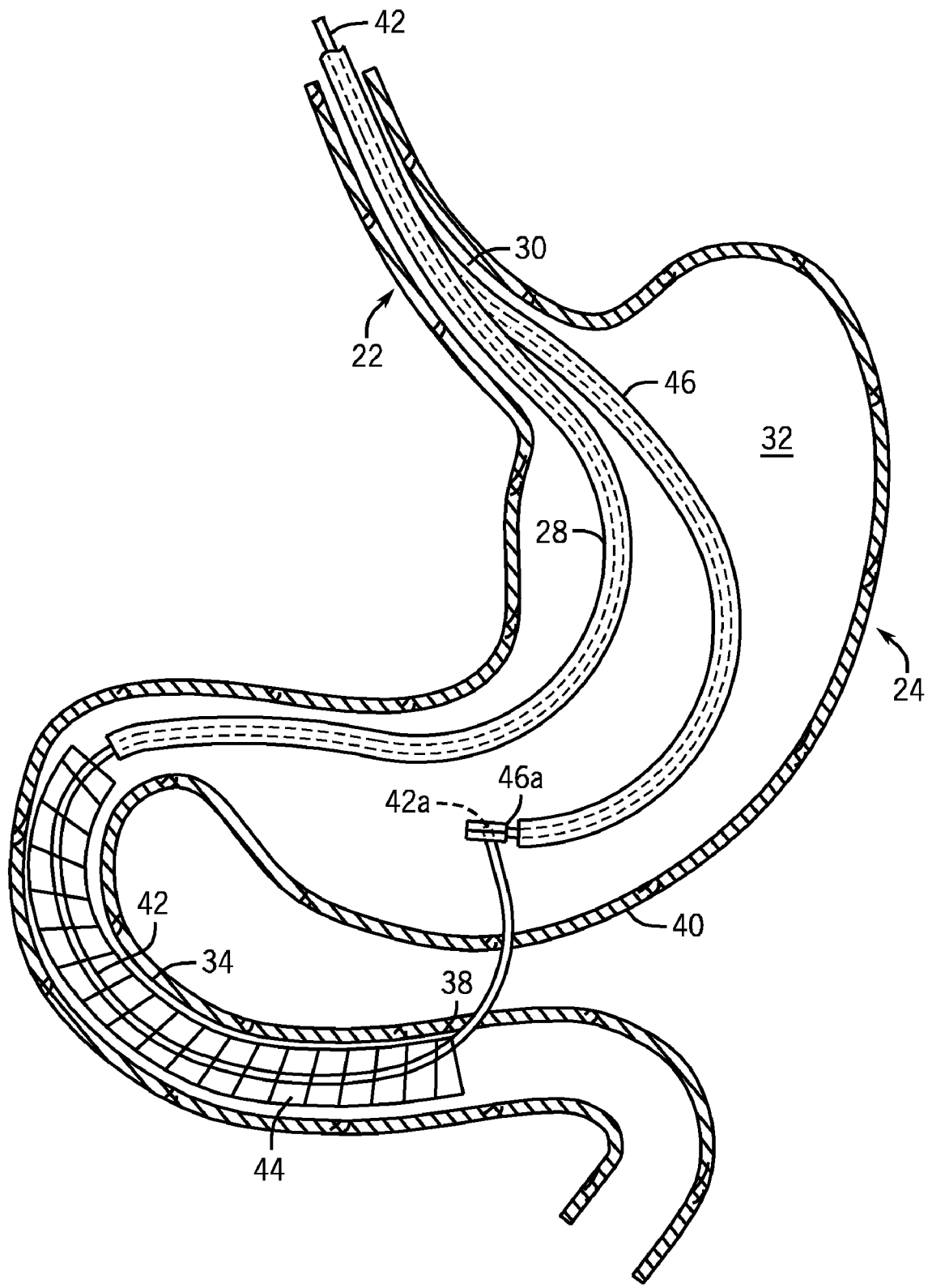
FIGS. 13-16 depict cross-sectional view of the gastrointestinal tract illustrating steps of the method in accordance with an alternative embodiment of the present invention.
Figure 14:
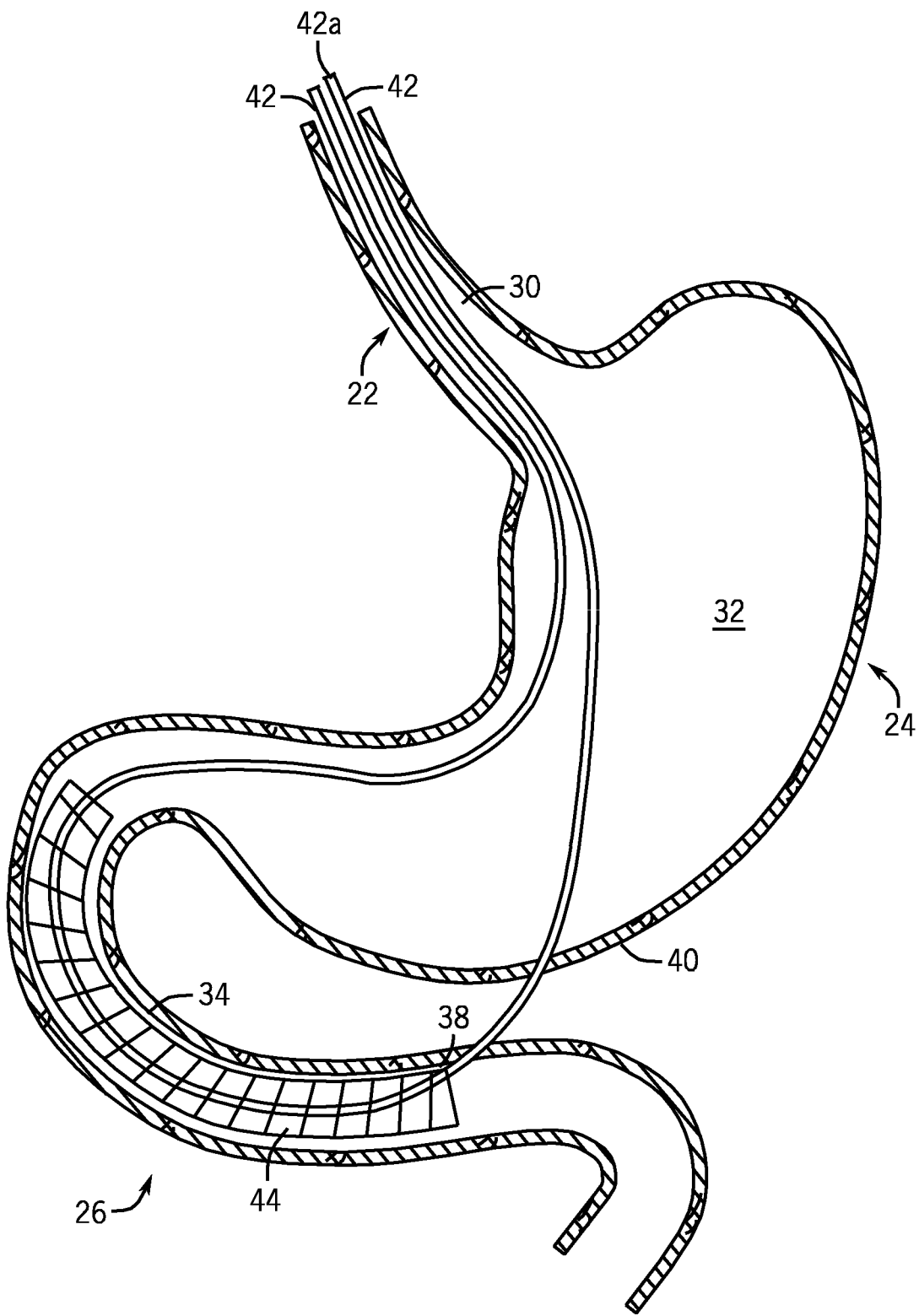
Figure 15:
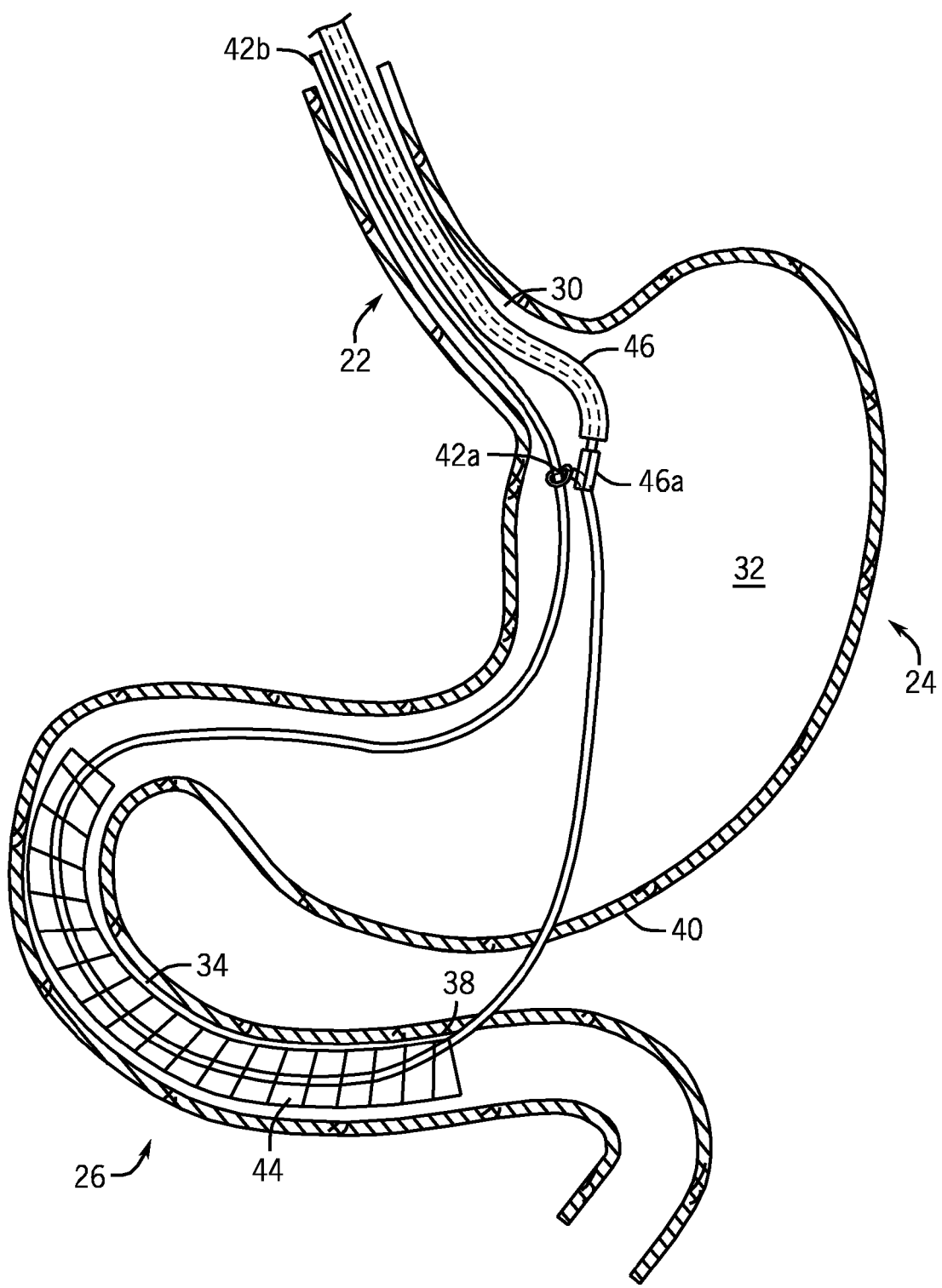

Reference is made to FIGS. 13-16 wherein a closed loop is formed (step 900) by securing the distal end 42a of anchoring device 42 to the body thereof in accordance with an alternative embodiment of the present invention. (For this embodiment, however, steps 200-800 are the same as identified in FIG. 1. Therefore, these steps will not be discussed herein.) In this alternative embodiment, step 900 is performed, but with some variation to achieve loop closure as follows. As indicated above with respect to step 900, the doctor performs this step using a second endoscope, i.e., endoscope 46. The doctor introduces endoscope 46 within the gastrointestinal tract in a similar manner as endoscope 28. The doctor uses a clamping mechanism 46a of endoscope 46, as known to those skilled in the art, to grasp distal end 42a of anchoring device 42. This is shown in FIG. 13. In this alternative embodiment, however, endoscope 46 is used to pull distal end 42a upwardly through stomach 24, esophagus 22 and out the patient's mouth. Now, both ends of anchoring device 42 extend out of the patients mouth as shown in FIG. 14 (mouth not shown).

At this point, endoscope 28 is removed. Note, however, that endoscope 28 could have been removed immediately after endoscope 46 clamped distal end 42a. Alternatively, the doctor may remove endoscope 28 immediately after the doctor removed guide wire 36, but before he/she clamps distal end 42a with clamping mechanism 46a. In this respect, the distal end 42a is sufficiently advanced into stomach lumen 32 to ensure that anchoring device does not retract though the pierced holes in stomach wall 40 and duodenum wall 38 while endoscope 28 is being removed. These are illustrative embodiments for deploying and retrieving both ends of anchoring device 42 out a patient's mouth. Those skilled in the art will know that there are other ways in which a doctor may properly deploy and obtain both ends of anchoring device 42 out of the patient's mouth.

Now, at the next step, the doctor will actually create a loop with anchoring device. In particular, the doctor makes a loose knot with distal end 42a around the upper portion of anchoring device 42 and uses clamp 46a of endoscope 46 to push the loose knot down esophagus 22 into stomach 24. The doctor will attempt to remove any excess slack by pushing the knot down the length of anchoring device 42. At the next step, the doctor uses clamp 46a to tighten the knot, and then cuts the anchoring device 46 above the knot to remove the residual portion of anchoring device 42. This is similar to the description of step 1000 set forth above. The doctor will then remove endoscope 46. While a knot is described herein, those skilled in the art, after reading this disclosure, know that a similar effect may be achieved use a ring for securing distal end 42a of anchoring device 42 to the body thereof within stomach lumen 32.

It will also be clear to one skilled in the art, after reading this disclosure, that the step of forming a closed loop with anchoring device 42 may be accomplished in other ways. For example, anchoring device 42 may be advanced as described in FIG. 1, but both ends of anchoring device 42 may be located within stomach lumen 32 and held in place using two independent endoscopes (clamps). These ends may be attached together using similar means described above, e.g., adhesive, Velcro like material, knot, etc. Thus, one end will be attached to a portion of anchoring device 42 as described above, but in this case, the portion will be the other end of anchoring device 42. In this respect, there will be no residual portion of anchoring device to cut and remove. The specific steps and the order in which they are performed may vary to form the closed loop in accordance with the method of present invention.

Alternatively, a closed loop may be formed with anchoring device 42 by securing it through the wall of duodenum 26 only. For example, duodenum 28 will be pierced in two separate points along duodenum wall 38 for the advancement of anchoring device 42. In this respect, anchoring device 42 will anchor (i.e., support) barrier device 42 by means of duodenum 26 (only). Those skilled in the art, after reading this disclosure, know that other variations exist to achieve the same result.

It will be clear to those skilled in the art that while one or two endoscopes are used for the embodiments described above, a single scope may be used with dual (or multiple) channels to achieve some or all of the steps described above (when an endoscope is required). It will be also clear to those skilled in the art, after reading this disclosure, that while the embodiments described above employ a method wherein anchoring device 42 is advanced through duodenum wall 38 and subsequently stomach wall 40, anchoring device 42 may alternatively be advanced through stomach wall 40 first and then through duodenum wall 38 (or other body portions to achieve desired results).

In the embodiments of the method described herein in accordance with the present invention, the position of barrier device 44 is actually maintained (secured) in place within duodenum lumen 34. That is, the distal end of anchoring device 42 (adjacent the pierced duodenum wall 38) prevents barrier device 44 from migrating downstream. Conversely, the proximal end of anchoring device 42 and the general anatomy of the gastrointestinal tract prevents barrier 44 from moving upstream within the gastrointestinal tract. In addition, it is noted that anchoring device 42 is used as the sole device or anchor for supporting barrier device 44 within the gastrointestinal tract. No other devices are needed to maintain the device within the gastrointestinal tract. The application of the anchoring device 42 as the sole support simplifies the procedure, and also reduces the incidence of tissue damage and inflammation.

Figure 16:
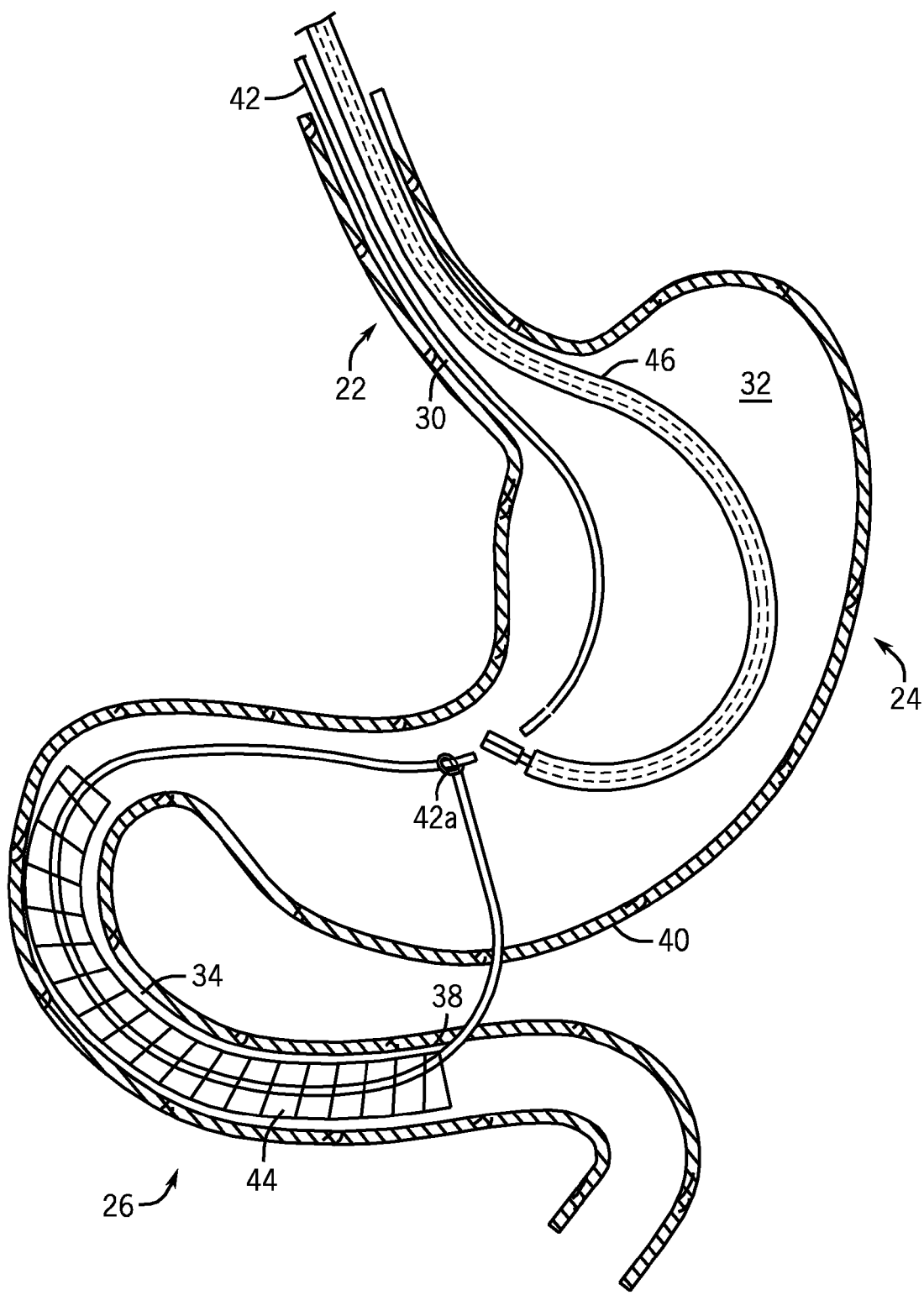
Figure 17:
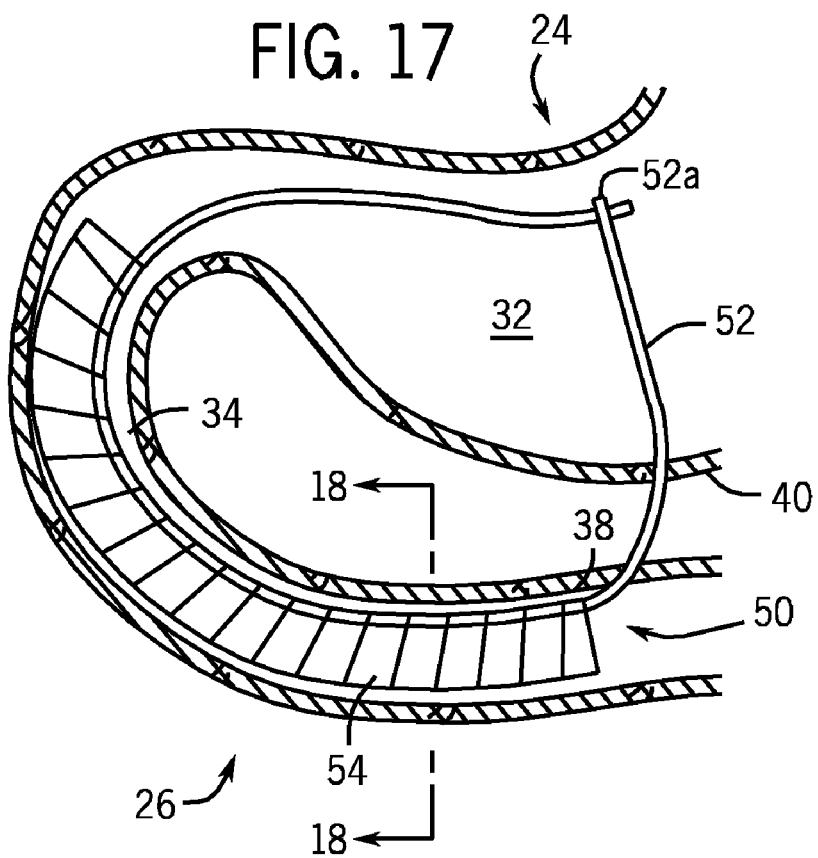
FIG. 17 depicts a cross-sectional view of the gastrointestinal tract similar to FIG. 16 but illustrating an alternative embodiment of the anchoring and barrier device.

FIG. 17 depicts a cross-sectional view of the gastrointestinal tract similar to FIG. 16 but illustrates an alternative embodiment of the anchoring device and barrier device. In particular, anchoring device 52 and barrier device 54 are shown deployed within the duodenum lumen 34. In this embodiment, however, anchoring device 52 and barrier device 54 are constructed as one integral component 50 that is delivered and secured in place in a similar manner as discussed above with respect to the method steps in FIG. 1.

In brief, a doctor will perform steps 200 and 300, and the doctor will then advance the integral component 50 over a guide wire via an endoscope through the stomach lumen and into the duodenum. In this case, barrier device 54, as an integral part of component 50, is compressed within the endoscope. The guide wire is removed (step 800) and, as integral component 50 is advanced, barrier device 54 will decompress/expand as it is released from the endoscope. Note that the integral component is sufficiently advanced to position barrier device 54 within the duodenum lumen 34. A loop is formed with anchoring device as described above with respect to step 900 as known by those skilled in the art. The doctor will remove the residual portion of anchoring device 52 of integral component 50 and then remove the endoscope from the gastrointestinal tract similar to steps 1000 and 1100, respectively. However, those skilled in the art know that variations in this method (that include different or additional steps or less steps) will produce the same results, i.e., deliver and secure barrier device 54 within the gastrointestinal tract. Note that anchoring device 52 and barrier device 54 (of integral component 50) may be constructed of the same or difference materials to achieve desired results. Examples of the materials are described above.

Figure 18:
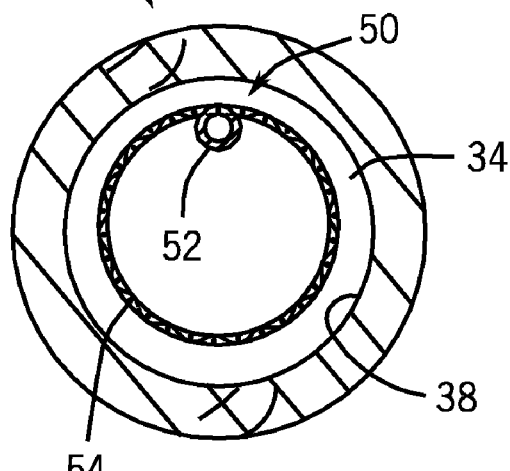
FIG. 18 depicts a cross-sectional view of the deployed barrier device illustrated in FIG. 17.

FIG. 18 depicts a cross-sectional view of the deployed barrier device 54 (as part of integral component 50) illustrated in FIG. 17.

As discussed above, the method for securing a barrier device within the gastrointestinal tract may alternatively employ a laparoscopic device for one or more of the steps of the method. That is, the laparoscopic device may be used to effect desired results without using an endoscope or may be used in combination with an endoscope. In one exemplary circumstance, a laparoscopic device may be used to assist in the threading of an anchoring device over a guide wire between the duodenum and stomach. That is, a doctor (endoscopic operator) would push the guide wire and/or needle out of the duodenum and the same or different doctor (i.e., laparoscopic operator) would grasp the guide wire with the laparoscopic device and pierce the stomach wall and place it in the stomach lumen. The laparoscopic device will also assist with the deployment of the anchoring device. That is, the doctor will pull the end of the anchoring device over the guide wire into the stomach lumen.

In another exemplary circumstance, a laparoscopic device may be used for loop closure within the stomach after the barrier device is properly positioned. That is, as known by those skilled in the art, the loop closure may be accomplished using the laparoscopic device to assist in tying the knot as described above. Once the anchoring device is secured, the tissue openings may be closed by the doctor. While two exemplary circumstances have been described hereinabove with respect to the laparoscopic device, those skilled in the art, after reading this disclosure, know that a laparoscopic device many be used to perform other the steps of the method for securing a barrier device within the gastrointestinal tract as disclosed in this application.

As discussed above, those skilled in the art, after reading this disclosure, know that the step of introducing the delivery apparatus may refer or include the step of advancing or introducing an endoscope, a guide wire, a laparoscopic device or other device individually or any combination of these devices. Also, the delivery apparatus disclosed herein may refer or include an endoscope, a guide wire, a laparoscopic device or other device individually or any combination of these devices.

It is to be understood that the disclosure teaches examples of the illustrative embodiments of the present invention and that many variations of the invention can easily be devised by those skilled in the art after reading this disclosure and that the scope of the present invention is to be determined by the following claims.

What is claimed is:

1. A method for creating an anchor within a gastrointestinal tract for supporting a barrier device therein, the gastrointestinal tract having a stomach and a duodenum, each having a wall defining a lumen, the method comprising:
   advancing an anchoring device through the duodenum wall and the stomach wall;
   threading the barrier device over the anchoring device and advancing the barrier device into the duodenum lumen; and
   forming a closed loop with the anchoring device for supporting the barrier device within the duodenum lumen.

2. The method of claim 1 wherein the anchoring device is a soft catheter.

3. The method of claim 1 wherein the barrier device is a flexible sleeve sized so as to substantially prevent the absorption of food products within the body lumen.

4. The method of claim 1 further comprising introducing a delivery apparatus into the gastrointestinal tract, wherein introducing a delivery apparatus includes advancing an endoscope within the stomach lumen.

5. The method of claim 4 wherein introducing a delivery apparatus further includes advancing a laparoscopic device into the duodenum lumen.

6. The method of claim 1 wherein the forming a closed loop including attaching an end of the anchoring device to a portion thereof.

7. The method of claim 1 further comprising introducing a delivery apparatus into the gastrointestinal tract, wherein introducing a delivery apparatus includes introducing a guide wire through the duodenum wall and stomach wall.

8. The method of claim 1 further comprising introducing a delivery apparatus into the gastrointestinal tract, wherein introducing a delivery apparatus includes advancing a laparoscopic device into the duodenum lumen.

9. A method for creating an anchor within a gastrointestinal tract for supporting a sleeve, the gastrointestinal tract having a stomach and a duodenum, each having a lumen and a wall, the method comprising:
   introducing a guide wire through the duodenum wall and stomach wall;
   advancing an anchoring device over the guide wire through the stomach wall and the duodenum wall;
   threading the sleeve over the anchoring device and advancing the sleeve into the duodenum lumen; and
   forming a closed loop with the anchoring device for supporting the sleeve within the duodenum lumen.

* * * * *